US012661214B2

(12) United States Patent
Kim et al.

(10) Patent No.: US 12,661,214 B2
(45) Date of Patent: Jun. 23, 2026

(54) ARTIFICIAL BLADDER SYSTEM HAVING DUAL SPACE DIVIDED BY PARTITION AND WIRELESS, NON-POWERED URINE FULLNESS SENSOR USING RFID TECHNOLOGY

(71) Applicants:Yonsei University Industry Foundation (Yonsei UIF), Seoul (KR); The Catholic University of Korea Industry-Academic Cooperation Foundation, Seoul (KR); Industry Academic Cooperation Foundation of Yeungnam University, Gyeongsan-si (KR); Chung Ang University Industry Academic Cooperation Foundation, Seoul (KR)

(72) Inventors: Jong Baeg Kim, Seoul (KR); U Syn Ha, Seoul (KR); Jin Ho Kim, Daegu (KR); Jung Wook Choi, Seoul (KR); Won Gun Koh, Seoul (KR); Gyu Jun Choi, Seoul (KR); Min Hyeong Kim, Gyeongju-si (KR); Won Keun Park, Seoul (KR); Jeong Hyeop Son, Seoul (KR)

(73) Assignees: Yonsei University Industry Foundation (Yonsei UIF), Seoul (KR); The Catholic University of Korea Industry-Academic Cooperation Foundation, Seoul (KR); Industry Academic Cooperation Foundation of Yeungnam University, Gyeongsan-si (KR); Chung Ang University Industry Academic Cooperation Foundation, Seoul (KR)

( * ) Notice: Subject to any disclaimer, the term of this patent is extended or adjusted under 35 U.S.C. 154(b) by 730 days.

(21) Appl. No.: 18/089,817

(22) Filed: Dec. 28, 2022

(65) Prior Publication Data

US 2023/0200974 A1     Jun. 29, 2023

(30) Foreign Application Priority Data

Dec. 28, 2021     (KR) ........................ 10-2021-0189371

(51) Int. Cl.
*A61F 2/04* (2013.01)
*G01L 9/00* (2006.01)

(52) U.S. Cl.
CPC ........... *A61F 2/042* (2013.01); *G01L 9/0072* (2013.01); *A61F 2250/0002* (2013.01); *A61F 2250/0013* (2013.01)

(58) Field of Classification Search
CPC .............. A61F 2/042; A61F 2250/0002; A61F 2250/0013; A61F 2/482; A61F 2/484;
(Continued)

(56) References Cited

U.S. PATENT DOCUMENTS

2010/0063237 A1* 3/2010 Dhruv ........................ C08J 3/20
                                                        528/32
2013/0172664 A1* 7/2013 Schmid ................... A61F 2/042
                                                        600/30
(Continued)

FOREIGN PATENT DOCUMENTS

EP          3895670          10/2021
KR     10-2009-0054427        5/2009
(Continued)

*Primary Examiner* — Thomas C Barrett
*Assistant Examiner* — Hanna L Pasqualini

(57) ABSTRACT

The present invention relates to an artificial bladder system having a double space divided by a partition wall and a wireless, non-powered urine fullness sensor using an RFID technology, which provides an artificial bladder system comprising: an outer wall that forms the outer shape of the artificial bladder, is inserted into the body, and has an inner (Continued)

(a)

(b)

space; a partition wall, wherein both ends are fixed to the inside of the outer wall, the inner space of the outer wall is divided into a double space of a urine reservoir and a working fluid space, and it is deformable according to amounts of the urine and the working fluid; and a urine fullness sensor installed in the working fluid space and sensing a urine fullness degree based on the deformation of the partition wall.

12 Claims, 3 Drawing Sheets

(58) Field of Classification Search
CPC ......... A61F 2/48; G01L 9/0072; G01L 1/144; G01L 19/086; A61B 5/208; A61B 5/0015; A61B 5/4851; A61B 2560/0204; A61B 5/205; A61B 5/202; A61B 5/204; H01G 5/011; H01G 5/06; H01G 5/16
See application file for complete search history.

(56) References Cited

U.S. PATENT DOCUMENTS

| | | | | |
|---|---|---|---|---|
| 2019/0091003 | A1 * | 3/2019 | Forsell | .................. A61F 2/0036 |
| 2020/0376266 | A1 * | 12/2020 | Toong | ................ A61N 1/36007 |

FOREIGN PATENT DOCUMENTS

| | | | | |
|---|---|---|---|---|
| KR | 10-2016-0090877 | | 8/2016 | |
| KR | 20160090877 | A * | 8/2016 | ........... H10F 39/026 |
| KR | 10-2020-0011653 | | 2/2020 | |
| KR | 10-2020-0136965 | | 12/2020 | |
| WO | WO-9316659 | A1 * | 9/1993 | ............. A61F 2/042 |
| WO | WO-2020022805 | A1 * | 1/2020 | ............. A61M 1/00 |

* cited by examiner (a)                    (b)

(a)        (b)        (c)

ARTIFICIAL BLADDER SYSTEM HAVING DUAL SPACE DIVIDED BY PARTITION AND WIRELESS, NON-POWERED URINE FULLNESS SENSOR USING RFID TECHNOLOGY

RELATED APPLICATION

This application claims the benefit of priority of Korean Patent Application No. 10-2021-0189371 filed on Dec. 28, 2021, the contents of which are incorporated herein by reference in their entirety.

FIELD AND BACKGROUND OF THE INVENTION

The present invention relates to an artificial bladder system, where the present invention comprises an artificial bladder structure having a double space divided by a partition wall, a urinary discharge principle using a working fluid, an operating principle for measuring a urine fullness degree inside a human body-implantable artificial bladder using radio frequency identification (RFID) wireless communication technology, a sensor structure, and a manufacturing method thereof. By development of an artificial bladder system capable of driving urine discharge and urine fullness degree sensing without implantation of power sources through the present invention, the lifespan of the artificial bladder can be increased, and the signals can be wirelessly exchanged without a procedure to connect the inside and outside of the body, thereby improving patients' life quality.

For patients who need existing bladder replacement, a procedure of taking the ureter out and wearing a urine bag, and a procedure of removing a part of the small intestine and manufacturing it in the form of a bladder are performed. However, the urine line is existing out of the body, thereby still significantly reducing the patient's life quality, and even if the bladder is made with the small intestine, it cannot perform the original bladder role.

Patients with underactive bladder do not recognize the urine fullness degree and do not discharge urine using bladder muscles. There are some existing technologies for developing artificial bladders to replace human bladders and measuring the urine fullness degree, but in the case of existing technologies, it is possible to generate negative pressure inside the human body-implantable artificial bladder, to cause fibrosis and adhesion problems, to lower the lifespan of the device and the patents' life quality by using separated power sources, or to cause malfunction of the sensor due to human motion.

SUMMARY OF THE INVENTION

It is an object of the present invention to provide an artificial bladder system capable of solving negative pressure generation inside the bladder by having a double-spaced artificial bladder structure and preventing fibrosis and adhesion problems, as the outer shape is not deformed.

It is another object of the present invention to provide an artificial bladder system capable of improving the lifespan of the device and patients' life quality by driving both urine discharge and a urine fullness sensor without power.

It is another object of the present invention to provide an artificial bladder system capable of reducing malfunction of a urine fullness sensor due to human movement by the sensor and the bladder structure.

In order to achieve the above objects, the present invention provides an artificial bladder system comprising: an outer wall that forms the outer shape of the artificial bladder, is inserted into the body, and has an inner space; a partition wall, wherein both ends are fixed to the inside of the outer wall, the inner space of the outer wall is divided into a double space of a urine reservoir and a working fluid reservoir, and it is deformable according to amounts of the urine and the working fluid; and a urine fullness sensor installed in the working fluid space within the outer wall and sensing a urine fullness degree based on the deformation of the partition wall.

In the present invention, the outer wall may be a hard outer wall formed from a biocompatible polymer and a curing agent, and the biocompatible polymer may be at least one of polydimethylsiloxane and perylene, where the weight ratio of the biocompatible polymer and the curing agent may be 10:1 or less.

In the present invention, the partition wall is formed by coating a reinforcing material which has high modulus and flexibility with polydimethylsiloxane, whereby it has no elastic restoring force and is easily deformable, where the length of the partition wall may be longer than the straight-line distance between both ends of the partition wall fixed to the outer wall. The reinforcing material may be a fabric made of a rigid material such as a glass or a metal or a polymer.

The artificial bladder system according to the present invention may further comprise: a valve installed in the ureter connected to the urine reservoir of the outer wall; and a valve installed in the urethra connected to the urine reservoir of the outer wall.

The artificial bladder system according to the present invention may further comprise: a working fluid reservoir connected to the working fluid space of the outer wall; a working fluid pump installed between the working fluid reservoir and the outer wall; and a valve installed at least one of a position between the working fluid reservoir and the outer wall and a position between the working fluid pump and the outer wall.

In the present invention, the volume of the working fluid reservoir is deformable according to the amount of the working fluid, and the working fluid pump is a manual pump operated by applying pressure, which can be driven without power.

The artificial bladder system according to the present invention may further comprise a reader that transmits and receives signals through wireless communication with the urine fullness sensor.

In the present invention, the reader is a patch-type reader attached to the outside of the body, which can have a self-alarm function, and deliver urine fullness information to a smartphone through Bluetooth.

In the present invention, the urine fullness sensor may transmit the urine fullness degree to the reader wirelessly and without power using the radio frequency identification (RFID) technology.

The urine fullness sensor according to a first embodiment of the present invention may be a capacitive type sensor based on capacitance changes.

In the present invention, the capacitive type sensor may comprise a capacitor composed of a first electrode and a second electrode.

In the present invention, the first electrode may be configured in the form of a flat plate buried and fixed to the inner surface of the outer wall; and the second electrode may be configured in a curved shape in which one end is fixed to the first electrode, and the remaining part is separated from the first electrode, but the distance from the first electrode is gradually widened toward the other end.

In the present invention, one end of the second electrode may be disposed toward the partition wall to be closer to the partition wall than the other end of the second electrode, and a plurality of capacitors may be installed, one of which may be disposed adjacent to the partition wall, and the other capacitors may be disposed gradually away from the partition wall.

In the present invention, the first electrode and the second electrode may each comprise a base layer such as a fiber layer made of a fabric, a metal layer coated with metal to surround the base layer, and a resin layer coated with polydimethylsiloxane to surround the whole layers.

In the present invention, the second electrode is deformed by contact with the partition wall, so that the capacitance change may occur while the widened portion of the second electrode contacts the first electrode, and when the contact with the partition wall is released, it may be restored to its original state as widened again.

The urine fullness sensor according to a second embodiment of the present invention may be a resistive type sensor based on resistance changes caused by contact resistance or piezoresistive properties.

In the present invention, the resistive type sensor may comprise a metal-patterned flexible substrate.

In the present invention, the metal-patterned flexible substrate may comprise a base layer made of polyimide or polydimethylsiloxane (PDMS), a metal pattern formed on the base layer, and a coating layer coated with polydimethylsiloxane to surround the base layer and the metal pattern.

In the present invention, the metal-patterned flexible substrate may have a shape in which one end is fixed to the outer wall, the other end is fixed to or in contact with the partition wall, and it is bent at a certain angle.

In the present invention, the metal-patterned flexible substrate is further bent to have a smaller angle due to the deformation of the partition wall, so that the resistance change may occur, and when the deformation of the partition wall is released, it may be restored to its original state as widened again.

The present invention has the following effects.

First, it has a double-spaced artificial bladder structure, so that it is possible to solve the negative pressure generation inside the bladder, and the outer shape is not deformed, so that it is possible to prevent fibrosis and adhesion problems.

Second, both the urine discharge and the urine fullness sensor are driven without power, so that it is possible to improve the lifespan of the device and the patients' life quality.

Third, due to the sensor and the bladder structure, it is possible to reduce malfunction of the urine fullness sensor by human movement.

4

Figure 4:
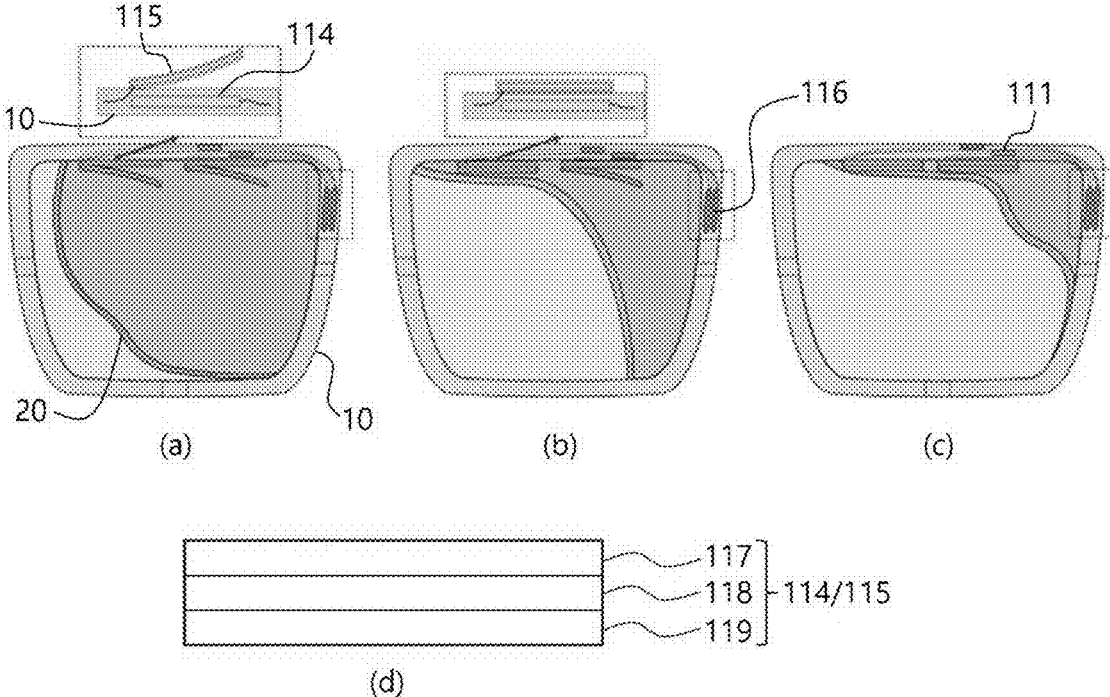

FIG. 4 shows a structure and an operating principle of the capacitive type urine fullness sensor according to the first embodiment of the present invention.

Figure 5:
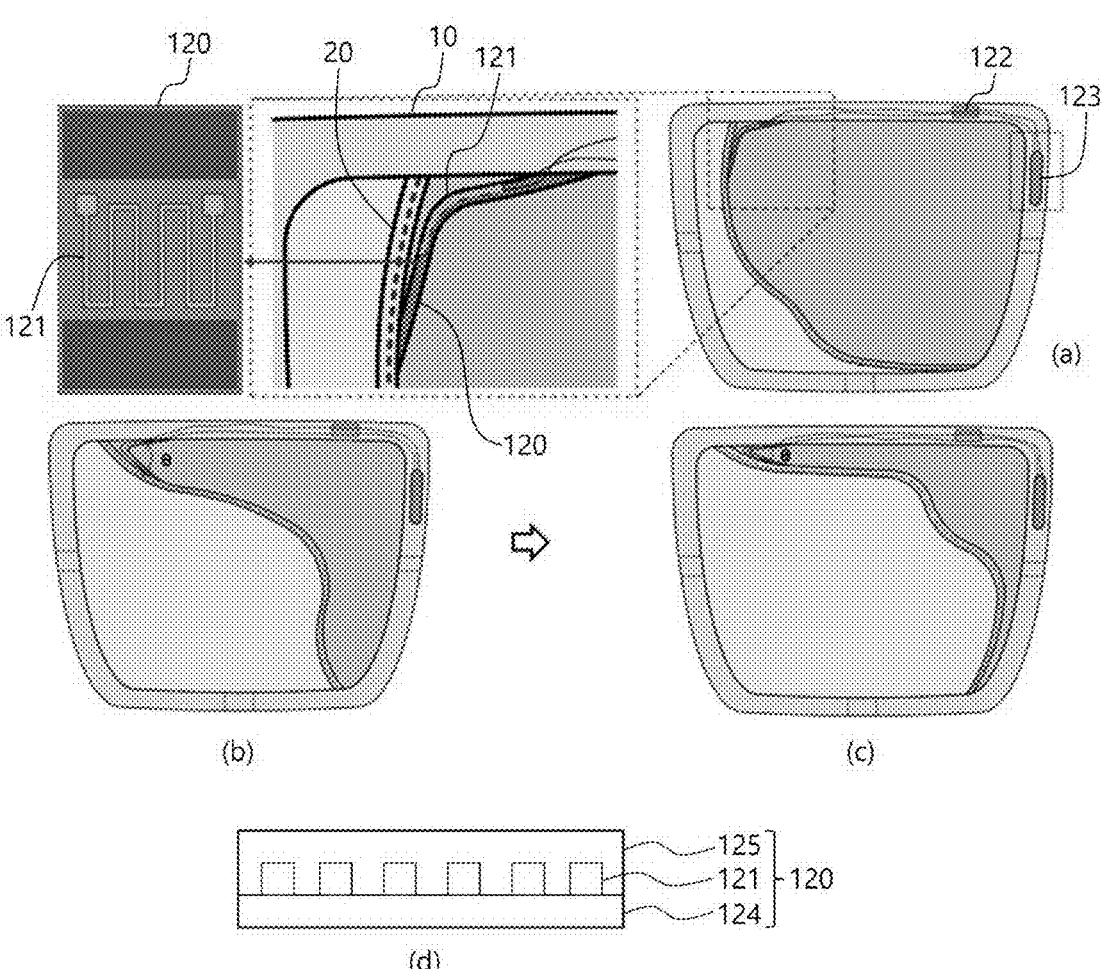

FIG. 5 shows a structure and an operating principle of a resistive type urine fullness sensor according to a second embodiment of the present invention.

DESCRIPTION OF SPECIFIC EMBODIMENTS OF THE INVENTION

Hereinafter, the present invention will be described in detail with reference to the accompanying drawings.

Referring to FIGS. 1 to 5, the artificial bladder system according to the present invention may be composed of an outer wall (10), a working fluid space (11), a urine reservoir (12), a ureter connection part (13), a urethra connection part (14), a working fluid connection part (15), a partition wall (20), a working fluid reservoir (30), a working fluid pump (40), a reader (50), coils (51, 116, 123), a ureter (60), a urethra (70), a pubis (80), a kidney (90), valves (100, 101, 102, 103), a capacitive type sensor (110), chips (111, 122), a resistor (112), a capacitor (113), a first electrode (114), a second electrode (115), a metal-patterned flexible substrate (120), a metal pattern (121), and the like.

FIG. 1(a) shows an artificial bladder structure with a double space. The artificial bladder may be composed of the outer wall (10) and the partition wall (20), and the artificial bladder may substantially mean the outer wall (10).

The outer wall (10) forms the outer shape of the artificial bladder, which may be inserted into the body, and have an internal space. The outer wall (10) may be inserted into the human body, and specifically fixed to the pubis (80). The outer wall (10) may be similar in shape and size to an actual bladder, but the shape and size, and the like of the outer wall (10) are not particularly limited, which may be appropriately set personally.

The inner space of the outer wall (10) may be composed of two spaces separated by the partition wall (20), that is, the working fluid space (11) and the urine reservoir (12). The outer wall (10) may be equipped with a ureter connection part (13) and a urethra connection part (14) installed on the urine reservoir (12) side, and a working fluid connection part (15) installed on the working fluid space (11) side.

The outer wall (10) may be a hard outer wall formed from a biocompatible polymer and a curing agent. The biocompatible polymer may be at least one of polydimethylsiloxane (PDMS) and perylene, and PDMS may be preferably used. The weight ratio of the biocompatible polymer and the curing agent may be 10:1 or less, for example 5±2:1, 5±1:1, or 5:1.

Conventionally, the weight ratio of the compatible polymer and the curing agent was about 10:1, but in the present invention, by increasing the curing agent ratio, a hard outer wall (10) can be formed, and accordingly, the outer wall (10) is not deformed, whereby it is possible to solve the fibrosis problem generated in the human body.

In this way, the outer wall (10) of the artificial bladder is made of PDMS and/or perylene, which are biocompatible materials, and the relatively hard outer wall (10) is made of PDMS with a high curing agent ratio, whereby the outer wall (10) is not deformed, so that the problem of fibrosis occurring within the human body can be reduced, and it can be easily fixed to the pubis (80) due to the hard outer wall (10).

The partition wall (20) has both ends fixed to the inside of the outer wall (10), divides the inner space of the outer wall (10) into a double space of a urine reservoir (12) and a working fluid space (11), and is deformable depending on the amounts of the urine and the working fluid. The partition wall (20) may be preferably disposed in a diagonal direction of the outer wall (10) for efficient urine fullness and discharge, and efficient operation of the urine fullness sensor.

The partition wall (20) is formed by coating a reinforcing material with polydimethylsiloxane (PDMS), whereby an elastic restoring force can be reduced. The PDMS is coated with spin coating to have a very thin thickness of a micrometer level, and there is a reinforcing material inside, whereby it may have improved durability to facilitate handling. Accordingly, the partition wall (20) has a structure that does not stretch while deforming well, whereby it is possible to prevent the negative pressure from being generated inside the artificial bladder due to the elastic restoring force, and it can be easily deformed according to the volume of urine. The reinforcing material may be a fabric made of a rigid material such as a glass or a metal or a polymer. For example, the reinforcing material may be a glass fiber fabric.

Both ends of the partition wall (20) may be fixed to the inner surface of the outer wall (10) using PDMS or the like. The length of the partition wall (20) may be longer than the straight-line distance between both ends of the partition wall (20) fixed to the outer wall (10), which may be, for example, 110 to 200%, 120 to 190%, 130 to 180%, 140 to 170%, or 150 to 160% relative to the straight-line distance. Since the urine fullness sensor senses the urine fullness degree based on the deformation of the partition wall (20), it is necessary to set an enough length of the partition wall (20) so that the electrodes of the sensor or the substrate can be fully deformed by the deformation of the partition wall (20).

In this way, the partition wall (20) inside the artificial bladder (10) distinguishes urine and the working fluid to form a double-spaced artificial bladder structure, and is manufactured by coating a reinforcing material with PDMS, whereby it has a structure that does not stretch while deforming well, so that it is possible to prevent the negative pressure from being generated inside the artificial bladder due to the elastic restoring force, and it can be easily deformed according to the volume of urine.

Figure 1:
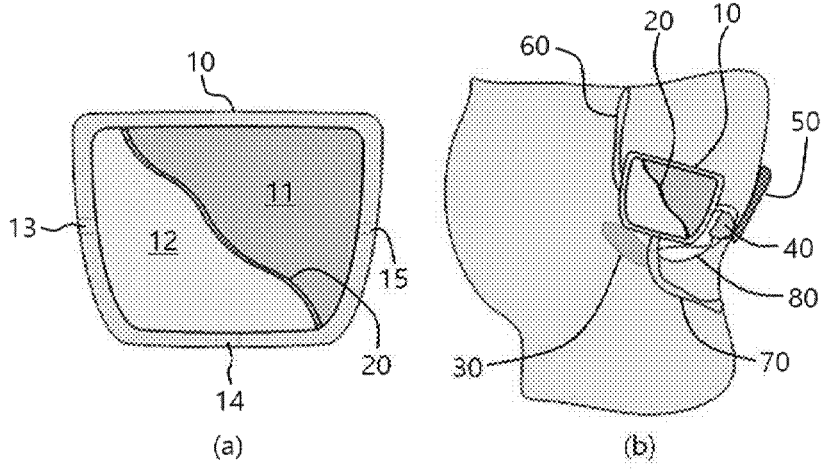
FIG. 1 shows a structure of an artificial bladder according to the present invention, and a human body insertion model of the artificial bladder system.

FIG. 1(*b*) shows a human body insertion model of the artificial bladder system. The artificial bladder system may be composed of an artificial bladder, which is an outer wall (10) having a partition wall (20), a working fluid reservoir (30), a working fluid pump (40), a reader (50), and the like, all of which can be implanted into the body, except for the reader (50). The ureter (60) and the urethra (70) connected to the urine reservoir (12) of the artificial bladder (10) may utilize actual ureter and urethra in the body as they are, or may also use an artificial ureter and an artificial urethra in the form of a tube.

The artificial bladder (10) may be fixed to the pubis (80). The working fluid reservoir (30) is located in the lower part (subcutaneous fat layer of the thigh) of the artificial bladder (10) and serves to store a working fluid for urine discharge. The working fluid reservoir (30) may be connected to the working fluid space (11) of the outer wall (10) through the working fluid connection part (15). The working fluid reservoir (30) is made of a material having low restoring force, whereby it can be deformed according to the amount of the working fluid, that is, the volume of the working fluid reservoir (30) can be deformed according to the amount of the working fluid. As the working fluid, water or the like may be used, and preferably deionized water may be used.

The working fluid pump (40) is firmly fixed to the pubis (80), thereby playing a role such that the patient may directly apply pressure to the skin to discharge urine at a desired time. The working fluid pump (40) may be installed between the working fluid reservoir (30) and the outer wall (10). The working fluid pump (40) is a manual pump operated by applying pressure, which may be driven wirelessly and without power. However, an automatic pump or the like may also be used as needed.

The reader (50) is a patch type reader attached outside the body, where the patch type reader (50) may be attached outside the skin. The reader (50) can transmit and receive signals through wireless communication with the urine fullness sensor, have a self-alarm function, and transmit urine fullness information to smartphones (52) of as a patient and the like through wireless communication such as Bluetooth™.

Figure 2:
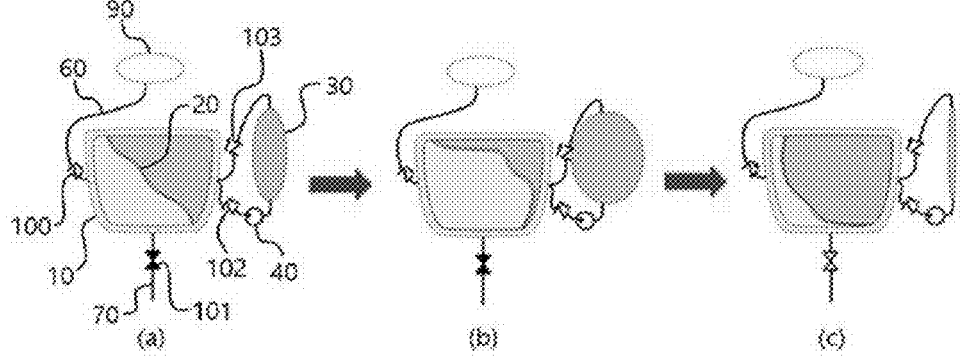
FIG. 2 shows an operating principle of urine discharge of an artificial bladder according to the present invention.

FIG. 2 shows an operating principle of the urine discharge system of the artificial bladder. FIG. 2(*a*) shows an initial state, FIG. 2(*b*) shows a urine fullness state, and FIG. 2(*c*) shows a urine discharge state.

A valve (100) may be installed at the anastomotic part of the ureter (60) connecting the artificial bladder (10) and the kidney (90), and preferably, a check valve for preventing backflow of urine may be used. That is, the urine only flows into the artificial bladder (10) from the kidney (90) and does not flow in the opposite direction.

A valve (101) of the anastomotic part of the urethra (70) replaces the human sphincter role. The valve (101) of the urethra (70) is not a check valve, where the opening and closing thereof can be adjusted manually or automatically, and it is closed in the initial state of FIG. 2(*a*) and the urine fullness state of FIG. 2(*b*), and it is opened only in the urine discharge state of FIG. 2(*c*).

The outer wall (10) and the working fluid reservoir (30) may be connected by a tube, and a valve (103) may be installed in the tube. The outer wall (10) and the working fluid pump (40) may be connected by a tube, and a valve (102) may be installed in the tube. Both valves (102, 103) may be check valves, and the valve (102) may be an on/off switch valve. That is, the working fluid can be circulated in only one direction. The valve may also be installed in a tube connecting the working fluid reservoir (30) and the working fluid pump (40) as needed.

In the initial state of FIG. 2(*a*), the partition wall (20) is arranged in an approximately diagonal direction, the inner space of the artificial bladder (10) is filled approximately half with urine and the working fluid, and the valve (101) is closed.

Referring to FIG. 2(*b*), the partition wall (20) of the artificial bladder is deformed according to the filling of urine to move the working fluid into the working fluid reservoir (30). Specifically, as urine flows thereto from the kidney (90), the partition wall (20) is pushed toward the working fluid space (11) and deformed, while the volume of the urine reservoir (12) of the artificial bladder (10) gradually increases. At the same time, as the volume of the working fluid space (11) gradually decreases, the working fluid in the working fluid space (11) is pushed out of the artificial bladder (11) and moves to the working fluid reservoir (30), and the volume of the working fluid reservoir (30) gradually expands. Finally, the urine fullness state of FIG. 2(*b*) is reached.

Referring to FIG. 2(*c*), when the urine is full, the patient can open manually the valve (101) acting as the sphincter at the desired time, automatically open it using a critical pressure valve, and apply a pressure to the working fluid pump (40) to fill the working fluid into the artificial bladder (10), whereby the urine is discharged. Specifically, when the valve (101) is opened and the working fluid pump (40) is operated in the urine fullness state of FIG. 2(*b*), the volume of the working fluid space (11) gradually increases, while the working fluid in the working fluid reservoir (30) is injected into the artificial bladder (10), and the partition wall (20) is deformed toward the urine reservoir (12), where the volume of the working fluid reservoir (30) gradually shrinks. At the same time, as the volume of the urine reservoir (12) gradually decreases, the urine in the urine reservoir (12) is pushed out of the artificial bladder (11) and discharged into the urethra (70). Finally, the urine discharge state of FIG. 2(c) is reached.

The urine fullness sensor according to the present invention serves to sense the urine fullness degree based on the deformation of the partition wall. The urine fullness sensor is preferably installed in the working fluid space to protect the sensor. The urine fullness sensor according to the present invention may transmit the urine fullness degree to the reader (50) wirelessly and without power using the radio frequency identification (RFID) technology.

Figure 3:
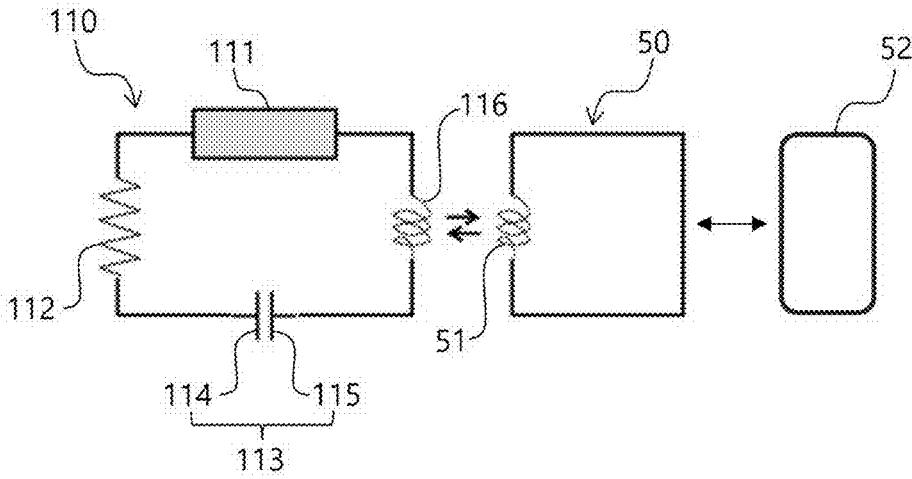
FIG. 3 shows an operating principle of a urine fullness sensor according to a first embodiment of the present invention.

FIG. 3 shows an operating principle of the urine fullness sensor. FIG. 3 shows a capacitive type urine fullness sensor based on capacitance changes according to the first embodiment of the present invention. The capacitive type sensor (110) of FIG. 3 may be composed of a chip (111), a resistor (112), a capacitor (113), a first electrode (114), a second electrode (115), and a coil (116). The chip (111) may be an RFID chip. The resistor (112) may be a resistor of an electric wire. The capacitor (113) is composed of a first electrode (114) and a second electrode (115). The coil (116) may transmit and receive mutually with the coil (51) of the reader (50) outside the body. The sensor may also be referred to as a tag.

As in FIG. 3, the present invention may transmit the urine fullness degree to the patient wirelessly and without power using the RFID technology. However, a power source such as a battery may be installed on the reader (50) side. As in FIG. 3, a circuit comprising an RLC (R: resistor, L: coil, C: capacitor) and a chip constituting the urine fullness sensor may be integrated inside the artificial bladder. The urine fullness sensor should measure the urine fullness degree by movement of the partition wall (20), because the generation of the force by the internal pressure change and the fluid is very small like the artificial bladder developed while minimizing the signal by the impact generated by movement of a person.

FIG. 4 shows processes that the capacitive type sensor of FIG. 3 is installed on the artificial bladder, and then operated. As described above, the capacitive type sensor (110) may comprise a capacitor (113) composed of a first electrode (114) and a second electrode (115). The capacitor (113) may be a variable capacitor.

Referring to the enlarged upper diagram of FIG. 4(a), the first electrode (114) may be configured in the form of a flat plate shape buried and fixed to the inner surface of the outer wall (10). Below the enlarged diagram, the first electrode (114) is shown as being on the inner surface of the outer wall (10), but as shown in the enlarged diagram, the first electrode (114) is preferably buried and fixed to the outer wall (10).

Referring again to the enlarged upper diagram of FIG. 4(a), one end of the second electrode (115) in the initial state before deformation is fixed to the first electrode (114), and the remaining part is separated from the first electrode (114), but it may be configured in a curved shape in which the gap with the first electrode (114) gradually widens toward the other end. That is, it may have a curved shape upward (downward when installed on the upper part of the outer wall (10)). The fixation of the two electrodes (114, 115) may be performed with PDMS or the like.

Referring to FIG. 4, one end of the second electrode (115) as fixed may be disposed toward the partition wall (20) to be closer to the partition wall (20) than the other end of the second electrode (115) as widened. As in FIG. 4, a plurality of capacitors (113) may be installed, and one of the capacitors (113) may be disposed adjacent to the partition wall (20), and the remaining capacitors (113) may be disposed gradually away from the partition wall (20).

Referring to FIG. 4 (d), the first electrode (114) and the second electrode (115) may each comprise a base layer (117) such as a fiber layer (corresponding to a core layer) made of a fabric, a metal layer (118) (a first coating layer or a first shell layer) coated with a metal so as to (preferably completely) surround the base layer (117), and a resin layer (119) (a second coating layer or a second shell layer) coated with polydimethylsiloxane (PDMS) to (preferably completely) surround the base layer (117) and/or the metal layer (118). The fabric may be a fiber material such as cotton or glass fiber, and the metal may be nickel (Ni) or the like. In the enlarged diagram of FIG. 4, the colors of the first electrode (114) and the outer wall (10) are the same, so that they are not distinguished, but the first electrode (114) is also coated with a PDMS resin layer. The PDMS resin layers on the surfaces of the electrodes facing each other may be thinly coated.

As in FIG. 4(a), the second electrode (115) is in a widened state in the initial state (before deformation), where this state is an off state.

As in FIG. 4(b), as the amount of urine in the artificial bladder (10) increases, the partition wall (20) contacts the first second electrode (115) disposed adjacent to the partition wall (20) while being deformed, and then the second electrode (115) is deformed due to contact with the partition wall (20), so that the capacitance change may occur, while the widened portion of the second electrode (115) contacts the first electrode (114). The state where the two electrodes (114, 115) are in complete contact with each other is an on state.

As in FIG. 4(c), as the amount of urine in the artificial bladder (10) further increases, the partition wall (20) may deform even the second electrode (115) disposed at the second position while being further deformed. In this way, the range of the urine fullness degree to be measured can be adjusted according to the attachment position, number, and size of the electrodes (114, 115).

When the working fluid flows into the artificial bladder (10) again and the urine is discharged, the partition wall (20) is deformed in the opposite direction again. When the contact between the second electrode (115) and the partition wall (20) is released, the second electrode (115) is restored to its original state, which can be widened again.

Referring to FIG. 4, a chip (111) and a coil (116) may be inserted into the outer wall (10). When a plurality of electrodes (114, 115) is installed, the same plurality of chips (111) and coils (116) may also be installed. However, unlike FIG. 4, even when a plurality of electrodes (114, 115) is installed, only one coil (116) may be installed while being connected in parallel. The resistor (112) may be a resistor of an electric wire.

As in FIG. 4, the fullness degree of urine can be measured through On/OFF of the signal of the tag (110) in the reader (50) by using, as a method of changing the capacitance of the sensor circuit, the resonant frequency change of the circuit. The variable capacitor is composed of two parallel plate electrodes, and one electrode (114) is buried in the outer wall (10) of the artificial bladder. The opposite electrode (115) is manufactured to have a curved shape by forming an electrode on a pre-strained PDMS substrate or a bent PDMS substrate manufactured through molding.

Since it can be easily deformed with the PDMS material, the capacitance increases by reducing the space between the two parallel plate electrodes (114, 115) by the movement of the partition wall (20) due to urine fullness. At this capacitance, the resonant frequency becomes close to the reader's resonant frequency, making it possible to transmit and receive information with a strong signal, and the reader (50) determines that the tag (110) in the Off state has turned On, whereby the urine fullness degree can be confirmed. The range of the urine fullness degree to be measured can be adjusted according to the attachment position, number, and size of the electrodes (114, 115).

FIG. 5 shows a resistive type urine fullness sensor based on a resistance change according to a second embodiment of the present invention, and shows processes operated after installation.

Referring to FIG. 5 (d), the resistive type sensor may comprise a metal- patterned flexible substrate (120). The metal-patterned flexible substrate (120) may comprise a base layer (124) (corresponding to the substrate) made of polyimide (PI) or polydimethylsiloxane (PDMS), a metal pattern (121) formed on the base layer (124), and a coating layer (125) (corresponding to a shell layer) coated with polydimethylsiloxane (PDMS) to surround the base layer (124) and the metal pattern (121).

Referring to FIG. 5, the metal pattern (121) may be formed in a zigzag shape in a vertical direction, and both ends of the metal pattern (121) may be configured as quadrangular pads for connection with electric wires. The metal pattern (121) may be composed of a double layer of a first metal layer for improving contact force and a second metal layer having excellent conductivity, where the first metal layer may be composed of titanium (Ti) or the like, and the second metal layer may be composed of gold (Au) or the like. For example, after forming a pattern with Ti on a PI substrate, an Au pattern can be formed directly on Ti, and then all the substrate and patterns can be coated with PDMS.

Referring to FIG. 5, the metal-patterned flexible substrate (120) may have a shape that one end is fixed to the outer wall (10), the other end is fixed to the partition wall (20), and it is bent at a predetermined angle θ). In the first diagram of FIG. 5, the upper and lower portions of the metal-patterned flexible substrate (120) are bonding areas.

As in FIG. 5(b), as the amount of urine in the artificial bladder (10) increases, the metal-patterned flexible substrate (120) fixed to or in contact with partition wall (20) is also deformed, while the partition wall (20) is deformed, and the angle (θ) of the metal-patterned flexible substrate (120) also changes to be small.

As in FIG. 5(c), as the amount of urine in the artificial bladder (10) further increases, the metal-patterned flexible substrate (120) is further deformed, while the partition wall (20) is further deformed, and the angle (θ) thereof also changes to be further small. When the amount of urine increases, the angle (θ) decreases and the resistance of the sensor increases.

In this way, the metal-patterned flexible substrate (120) is further bent such that the angle (θ) becomes smaller due to the deformation of the partition wall (20), whereby the resistance change may occur, and when the deformation of the partition wall (20) is released, the original state may be restored and widened again.

Referring to FIG. 5, in the resistive type urine fullness sensor according to the second embodiment, a chip (122) and a coil (123) may be installed, and they may be inserted into the outer wall (10).

A chip for signal processing, such as a transponder, may be added to the resistive type urine fullness sensor. Depending on the resistance change, the voltage generated in the transponder changes, and the signal transmitted from the tag changes, where the urine fullness degree can be continuously measured.

As in FIG. 5, a metal-patterned flexible substrate (120) may be attached between the outer wall (10) and the partition wall (20) of the artificial bladder so that the resistance is changed by deformation. With the deformation of the partition wall (20), the patterned metal (121) receives tensile or compressive deformation by bending, whereby the resistance changes. As the urine is filled, the resistance changes continuously, where the urine fullness degree can be continuously confirmed.

Advantages of the artificial bladder and the urine fullness sensor proposed in the present invention, which are distinguished from existing studies and inventions, and the like, are as follows.

First, it has a double-spaced artificial bladder structure, whereby it is possible to solve the negative pressure generation inside the bladder, and the outer shape is not deformed, whereby it is possible to prevent fibrosis and adhesion problems.

Second, both the urine discharge and the urine fullness sensor are driven without power, whereby the lifespan of the device and the patient's life quality can be improved.

Third, with the sensor and the bladder structure, it is possible to reduce malfunction of the urine fullness sensor by human movement.

In the case of the present invention, it is possible to improve the fibrosis and adhesion problems that may occur in existing human body-implantable artificial bladders with an artificial bladder having a new structure. Then, in consideration of the malfunction of the sensor due to human movement, it has a sensor operating principle that minimizes it. In addition, it comprises one optimized artificial bladder system model by integrating all the urine storage function, urine discharge function, and urine fullness sensing function.

EXPLANATION OF REFERENCE NUMERALS

10: outer wall, 11: working fluid reservoir, 12: urine reservoir, 13, ureter connection part, 14: urethral connection part, 15: working fluid connection part, 20: partition wall, 30: working fluid bag, 40: working fluid pump, 50: reader, 51, 116, 123: coil, 60: ureter, 70: urethra, 80: pubis, 90: kidney, 100, 101, 102, 103: valve, 110: capacitive type sensor, 111, 122: chip, 112: resistor, 113: capacitor, 114: first electrode, 115: second electrode, 120: metal-patterned flexible substrate, 121: metal pattern

What is claimed is:

1. An artificial bladder system comprising:
an outer wall that forms an outer shape of the artificial bladder, is configured to be inserted into a body, and the outer wall has an inner space;
a partition wall, wherein both ends are fixed to an inside of the outer wall, the inner space of the outer wall is divided into a double space of a urine reservoir and a working fluid space, and the partition wall is deformable according to amounts of an urine and a working fluid; and a urine fullness sensor installed in the working fluid space and sensing a urine fullness degree based on a deformation of the partition wall wherein the urine fullness sensor is a capacitive type sensor based on capacitance changes, wherein the capacitive type sensor comprises a capacitor composed of a first electrode and a second electrode, wherein the first electrode is configured in the form of a flat plate buried and fixed to an inner surface of the outer wall; and the second electrode is configured in a curved shape in which a first end of the second electrode is fixed to the first electrode, and a remaining part of the second electrode except the first end is separated from the first electrode, but the distance from the first electrode is gradually widened toward a second end opposite to the first end of the second electrode.

2. The artificial bladder system according to claim 1, wherein the outer wall is a hard outer wall formed from a biocompatible polymer and a curing agent, and the biocompatible polymer is at least one of polydimethylsiloxane and perylene, where a weight ratio of the biocompatible polymer and the curing agent is 10:1 or less.

3. The artificial bladder system according to claim 1, wherein the partition wall is formed by coating a reinforcing material with polydimethylsiloxane, and the length of the partition wall is longer than the straight-line distance between both ends of the partition wall fixed to the outer wall.

4. The artificial bladder system according to claim 1, further comprising:

a first valve configured to be installed in an ureter connected to the urine reservoir; and a second valve configured to be installed in a urethra connected to the urine reservoir.

5. The artificial bladder system according to claim 1, further comprising:

a working fluid reservoir connected to the working fluid space of the outer wall;

a working fluid pump installed between the working fluid reservoir and the outer wall;

and a valve installed at least one of a position between the working fluid reservoir and the outer wall and a position between the working fluid pump and the outer wall.

6. The artificial bladder system according to claim 5, wherein the working fluid pump is a manual pump operated by applying pressure, which is driven wirelessly and without power.

7. The artificial bladder system according to claim 1, further comprising a reader that transmits and receives signals through wireless communication with the urine fullness sensor.

8. The artificial bladder system according to claim 7, wherein the reader is a patch-type reader configured to be attached to the outside of the body, the reader has a self-alarm function, and the reader delivers urine fullness information to a smartphone through wireless communication.

9. The artificial bladder system according to claim 7, wherein the urine fullness sensor transmits the urine fullness degree to the reader wirelessly and without power using a radio frequency identification (RFID) technology.

10. The artificial bladder system according to claim 1, wherein the first end of the second electrode is disposed toward the partition wall to be closer to the partition wall than the second end of the second electrode, and a plurality of capacitors is installed, one capacitor of the plurality of capacitors is disposed adjacent to the partition wall, and other capacitors of the plurality of capacitors are disposed gradually away from the partition wall.

11. The artificial bladder system according to claim 10, wherein the first electrode and the second electrode each comprise a base layer, a metal layer coated with metal to surround the base layer, and a resin layer coated with polydimethylsiloxane to surround the base layer and the metal layer.

12. The artificial bladder system according to claim 11, wherein the second electrode is deformed by contact with the partition wall, so that the capacitance changes occur while a widened portion of the second electrode contacts the first electrode, and when the contact with the partition wall is released, the second electrode is restored to an original state of the second electrode to be widened again.

* * * * *